United States Patent
Cooper et al.

[19]

[11] Patent Number: 5,882,342
[45] Date of Patent: Mar. 16, 1999

[54] SAFETY MEDICAL SYRINGE WITH RETRACTABLE NEEDLE

[75] Inventors: Donald L Cooper, Upper Arlington; Douglas E Boyd, Dublin; Roger W Smith, Grove City; Elgene R Gillespie, Canton, all of Ohio

[73] Assignee: Safety Medical Manufacturing, Inc, Bushnell, Fla.

[21] Appl. No.: 837,276

[22] Filed: Apr. 11, 1997

[51] Int. Cl.$^6$ .................................................. A61M 5/00
[52] U.S. Cl. .......................... 604/195; 604/110; 604/198
[58] Field of Search .................................. 604/195, 192, 604/198, 263, 110, 187

[56] References Cited

U.S. PATENT DOCUMENTS

| | | | |
|---|---|---|---|
| 4,728,320 | 3/1988 | Chen | 604/110 |
| 4,838,863 | 6/1989 | Allard et al. | 604/110 |
| 4,921,486 | 5/1990 | De Chellis et al. | 604/110 |
| 4,950,241 | 8/1990 | Ranford | 604/110 |
| 4,973,316 | 11/1990 | Dysarz | 604/110 |
| 4,978,343 | 12/1990 | Dysarz et al. | 604/110 |
| 5,000,738 | 3/1991 | Lavallo et al. | 604/110 |
| 5,019,044 | 5/1991 | Tsao | 604/110 |
| 5,024,616 | 6/1991 | Ogle, II | 604/110 |
| 5,049,133 | 9/1991 | Pascual | 604/110 |
| 5,064,419 | 11/1991 | Gaarde | 604/110 |
| 5,180,370 | 1/1993 | Gillespie | 604/110 |
| 5,188,599 | 2/1993 | Botich et al. | 604/110 |
| 5,190,526 | 3/1993 | Murray et al. | 604/110 |
| 5,267,961 | 12/1993 | Shaw | 604/110 |
| 5,389,076 | 2/1995 | Shaw | 604/110 |
| 5,423,758 | 6/1995 | Shaw | 604/110 |
| 5,542,927 | 8/1996 | Thorne et al. | 604/110 |

*Primary Examiner*—John D. Yasko
*Attorney, Agent, or Firm*—Paul E Milliken; Lee A Germain

[57] ABSTRACT

A syringe for giving medical injections which has an internal mechanism for retracting the needle into the syringe after the injection has been given and locking the needle and plunger inside the barrel of the syringe to reduce the risk of accidental needle pricks. In one embodiment the needle is retracted by a tension spring into a compartment inside a hollow plunger and in the other embodiment the needle is propelled by a compressed spring into a compartment within the plunger. In both embodiments, the interior of the hollow plunger is hydraulically sealed off by a barrier from the fluid chamber of the syringe to prevent fluid from entering the interior of the hollow plunger.

32 Claims, 4 Drawing Sheets

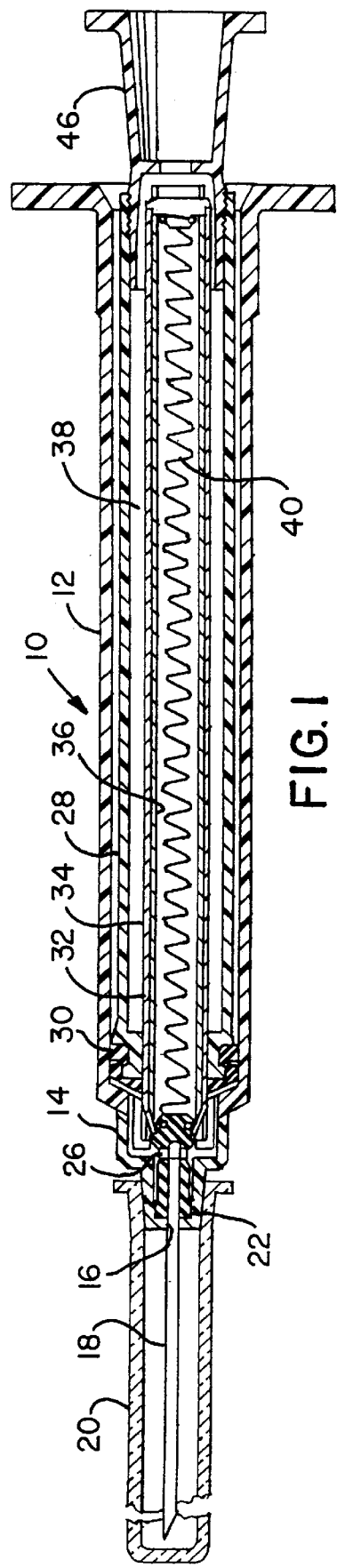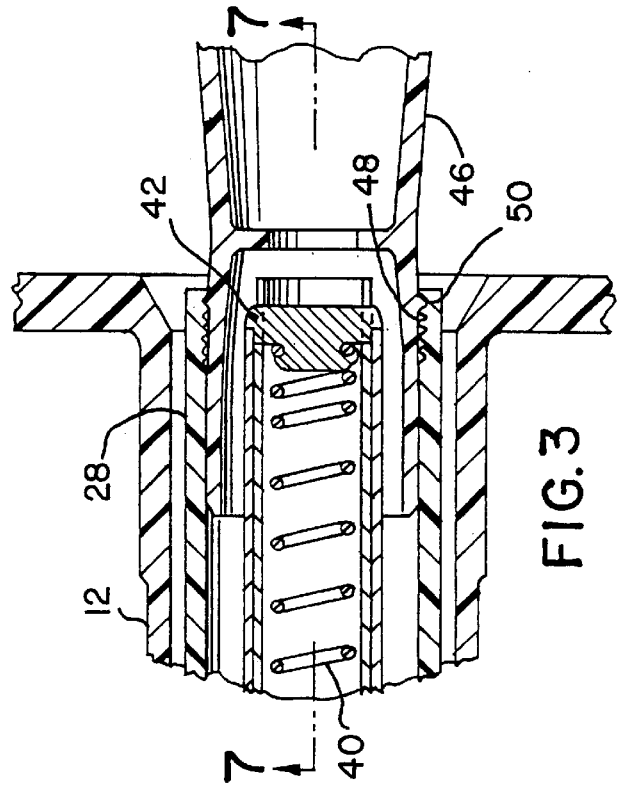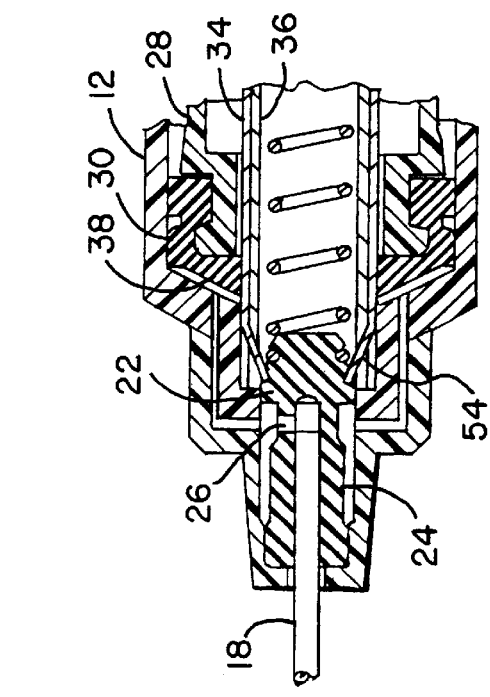

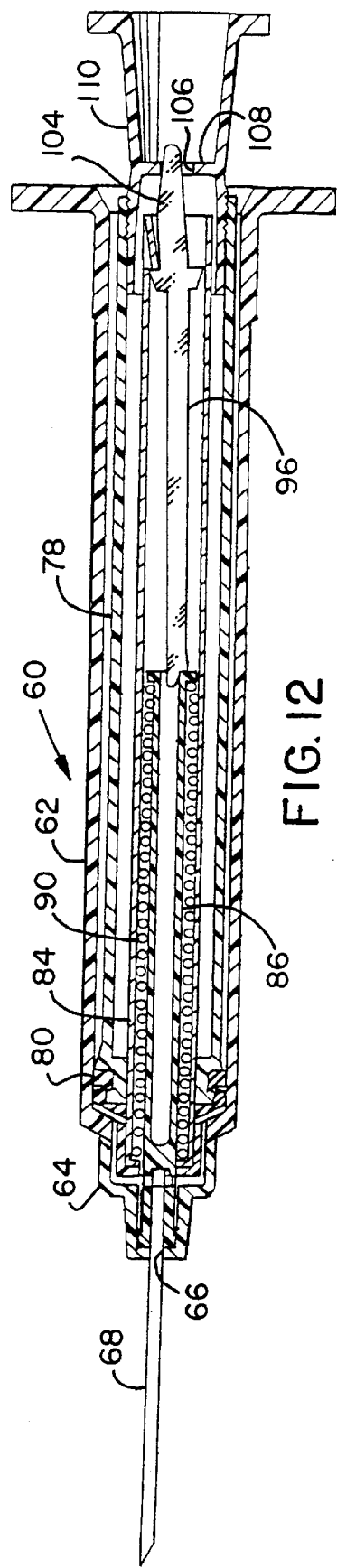
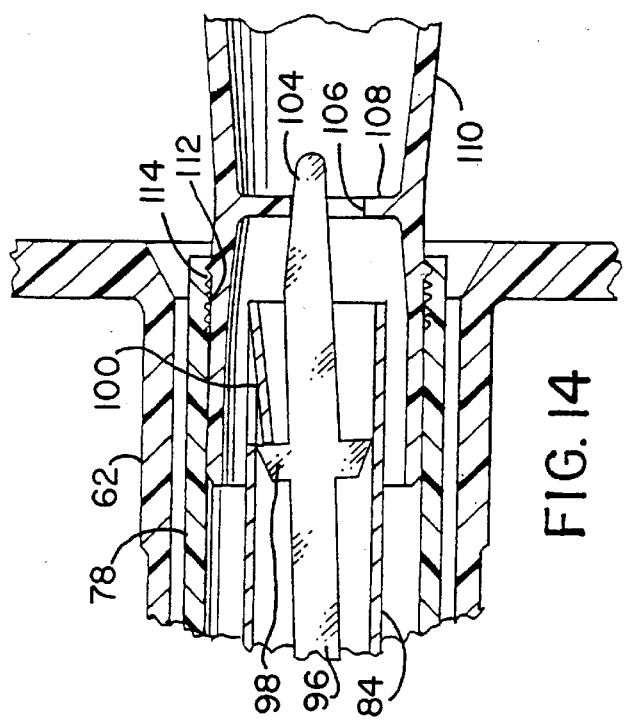
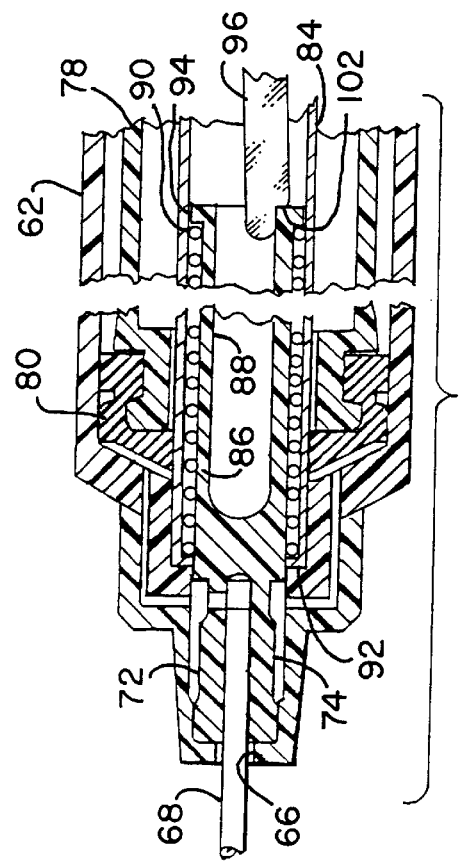

SAFETY MEDICAL SYRINGE WITH RETRACTABLE NEEDLE

FIELD OF THE INVENTION

This invention relates generally to medical syringes such as hypodermic syringes and in particular to the type having retractable needles which are withdrawn into the barrel and/or plunger after an injection has been given, thereby preventing accidental needle pricks which could transmit AIDS, hepatitis and other infectious diseases.

BACKGROUND OF THE INVENTION

In the past various attempts have been made to design hypodermic syringes with retractable needles. Typical examples of such devices are shown in U.S. Pat. Nos. 4,838,863; 5,019,044; 5,064,419; 4,950,241; and 4,978,343.

Some of these patents show the needle retracted into a hollow piston or barrel of a syringe either manually or by a spring which is biased to move the needle into a stored position either within a hollow piston or at least within the barrel of a hypodermic syringe. Such devices are only as effective and reliable as the design of the mechanisms used to retract the needle and some mechanisms may either fail to retract the needle completely or may fail to retain the needle in a retracted position.

The present invention is a further development of the concept shown in prior U.S. Pat. No. 5,180,370 issued to E. R. Gillespie which uses a hollow plunger in a medical syringe as a needle storage compartment when the needle has been retracted inside the syringe after an injection has been given. One primary advantage of the hollow plunger is that the needle can be in the stored or retracted position inside the plunger when the plunger is pressed into the barrel. In other patents which do not show a hollow plunger, the plunger must either be left protruding from the rear end of the barrel after needle retraction or in some instances the protruding portion of the plunger is broken off at the rear end of the barrel. Either option is not as desirable as having substantially all of the plunger contained inside the barrel after the needle has been retracted.

Both the prior Gillespie patent (U.S. Pat. No. 5,180,370) and the present invention provide a means of hydraulically sealing off the interior of the hollow plunger from the fluid chamber of the syringe.

The prior Gillespie patent mentioned above, uses an end cover member over the front end to the plunger to seal of the interior of the hollow plunger from the fluid chamber.

The present invention uses an elongated tube structure for sealing off the interior of the plunger from the fluid chamber and for receiving a bias spring for retracting a needle and needle mounting plug into the syringe.

Many additional patents have been issued on retractable needles since the prior Gillespie patent. Typical examples of such patents are U.S. Pat. No. 5,188,599 (Botich et al.); U.S. Pat. No. 5,190,526 (Murray et al); and three U.S. Pat. Nos. 5,267,961; 5,389,076; and 5,423,758 (all of which are issued to T. R. Shaw).

OBJECTS OF THE INVENTION

It is a primary object of this invention to provide a hypodermic syringe with a retractable needle which is simple, reliable, will retract rapidly and which will securely retain the needle in the retracted position.

Another object of this invention is to provide a hypodermic syringe with a retractable needle wherein the plunger or piston remains in a depressed position within the barrel of the syringe after the needle is retracted into the plunger.

A still further object of this invention is to provide a hypodermic syringe with a retractable needle which is inexpensive to manufacture and easy to use.

An even further object of this invention is to provide a hypodermic syringe with a retractable needle in which the parts of the syringe which are exposed to injection fluids are made of materials which will not chemically react with the injection fluids, These and other objects of the invention will become more fully apparent in the following specification and the attached drawings.

SUMMARY OF THE INVENTION

This invention is a safety medical syringe comprising: a hollow barrel for containing a fluid having a rear end opening and a front end opening and a fluid chamber therein extending between said openings, a hollow plunger mounted in the fluid chamber of the barrel and axially moveable back and forth between the front and rear end opening of the barrel, for the intake and expulsion of fluid from the fluid chamber, the plunger containing an axial needle receiving chamber therein and the plunger having a rear end portion extending out of the rear end opening of the barrel, sealing means on the plunger, engaging wall surfaces of the barrel within the fluid chamber to prevent fluid from leaking out of the rear end of the barrel, barrier means associated with the plunger to hydraulically separate the fluid chamber from the needle receiving chamber to prevent fluid from the fluid chamber from entering the needle receiving chamber, a hollow needle temporarily mounted at the front end of the barrel and protruding therefrom, the barrel and needle defining a fluid path means between the fluid chamber and the interior of the hollow needle to permit fluid to flow from the fluid chamber through the needle when the plunger is moved toward the front end of the barrel, bias means within the barrel associated with needle urging the needle to a retracted position in the interior of the needle receiving chamber, retaining means fixed relative to the barrel for preventing the needle from moving into the needle receiving chamber until fluid has been expelled from the fluid chamber, and release means associated with the retaining means for releasing the retaining means to permit the bias means to move the needle into the needle receiving chamber after the fluid has been expelled from the fluid chamber.

DESCRIPTION OF THE DRAWINGS

FIG. 1 is an axial cross-sectional view of a syringe illustrating one embodiment of the invention with the plunger substantially depressed and the needle protruding from the front end of the barrel;

FIG. 2 is an enlarged fragmentary cross-sectional view of the front end of the syringe shown in FIG. 1;

FIG. 3 is an enlarged fragmentary cross-sectional view of the rear end of the syringe shown in FIG. 1;

FIG. 12 is an axial cross-sectional view of a syringe illustrating another embodiment of the invention using a compression spring with the plunger substantially depressed and the needle protruding from the front end of the barrel;

FIG. 13 is an enlarged fragmentary cross-sectional view of the front end of the syringe shown in FIG. 12; and FIG. 14 is an enlarged fragmentary cross-sectional view of the rear end of the syringe shown in FIG. 12.

DESCRIPTION OF THE PREFERRED EMBODIMENTS

Figure 4:
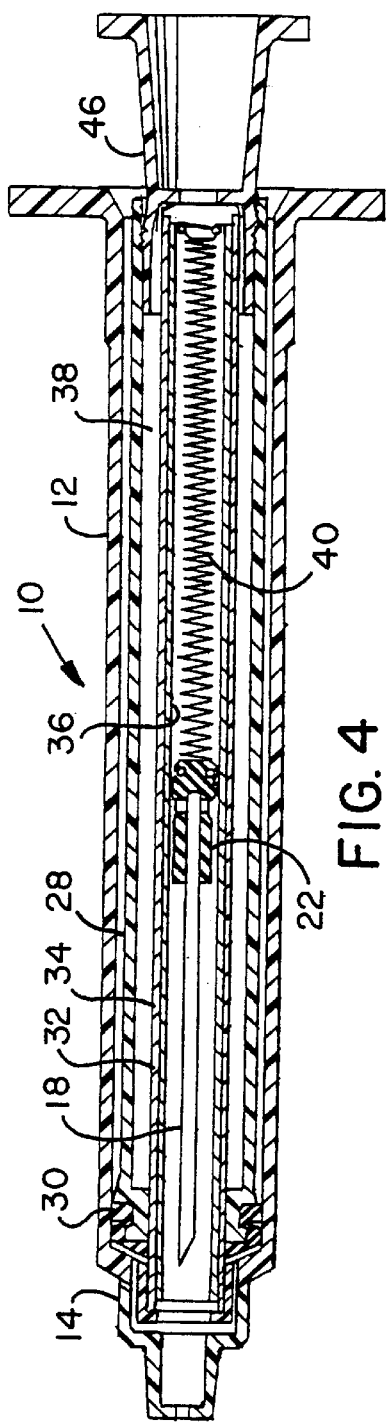
FIG. 4 is an axial cross-sectional view of the syringe shown in FIG. 1 with the needle and needle housing in the retracted position inside a tubular assembly within a hollow plunger.

Referring now to the drawings and in particular to FIGS. 1 through 3, a medical syringe is indicated generally by the numeral 10. The syringe 10 has a hollow cylindrical barrel 12 which is open at the rear end and covered at the front end by a front end cap 14 which is secured adhesively or by other suitable means to the barrel 12. The end cap 14 has a center hole 16, through which a hollow needle 18 projects and which is covered by a sheath 20 which fits over the end cap 14.

The needle 18 is secured in a needle mounting plug or housing 22 which together comprise a needle assembly 24 which is initially mounted with the needle housing 22 inside the end cap 14 in sealing engagement therewith. The housing 22 is preferably made of elastomeric material which is molded on the needle 18. The needle 18 and housing 22 have a passageway 26 providing fluid communication between the interior of the needle 18 and the interior of the end cap 14.

The barrel 12 contains an axially slidable plunger 28 which carries an annular seal ring 30 on the front end thereof. An axial tube assembly 32 has an outer tube 34 having its front end sealing mounted in the barrel 12 at the front end thereof and an inner tube 36 slidably mounted within the outer tube 34.

Both the outer tube 34 and the inner tube 36 are made preferably of metal such as brass, aluminum or stainless steel. They can both be made of the same metal or each of different metals. The outer surface of the outer tube 34 may be coated with a barrier coating such as a polymer or other benign material to prevent any chemical reaction between any fluid in the syringe and the metallic outer tube 34.

As may be seen in FIGS. 1 and 2, the annular seal 30 seals against both the interior of the barrel 12 and the exterior of the outer tube 34 which form an annular fluid chamber 38 therebetween.

When the plunger 28 is depressed the seal 30 prevents fluid from leaking to the rear end of the barrel 12 and forces the fluid to the front end of the barrel and through the passageway 26 into the hollow needle 18 through which it is expelled when an injection is given.

Because of the manner is which the outer tube 34 is sealingly mounted in the barrel 12 and with the needle housing 22 sealing against the front end of the barrel 12, all fluid in the fluid chamber 38 is hydraulically sealed off from the interior of the tube assembly 32.

As shown in FIGS. 1 and 2 a tension spring 40 is mounted inside the inner tube 36 with its front end attached to the needle housing 22 and its rear end attached to a rear retainer clip 42 which is held in a slot 44 in the rear end of the inner tube as shown in FIGS. 3 and 7 through 9.

As shown in FIGS. 1 and 3, the plunger 28 has a rear end cap 46 telescopingly mounted at the rear end thereof. An inner wall surface at the rear end of the plunger 28 has annular serrations 48 which are engaged by an annular rib 50 on end cap 46 which resists relative axial movement between the plunger 28 and the end cap 46.

This enables the plunger 28 to be moved to the front end of the barrel 12 to expel all fluid from the syringe before there is any relative movement between the plunger 28 and end cap 46. Once the front end of the plunger 28 contacts the front end of the barrel 12, the rib 50 of the end cap 46 starts moving across the serrations 48 and overcomes the resistance of the serrations to permit the end cap to 46 move forward relative to the plunger 28 thereby permitting a flange 52 to bear against the rear end of the inner tube 36 as shown in FIG. 6, thereby causing it to move forward so that the front end of the inner tube 36 forces tabs 54 radially outwardly from their retaining position against the needle housing 22, thereby releasing the housing and permitting the tension spring 40 to retract the needle housing 22 and needle 18 inside the inner tube 36 as shown in FIGS. 4 and 5.

Figure 6:
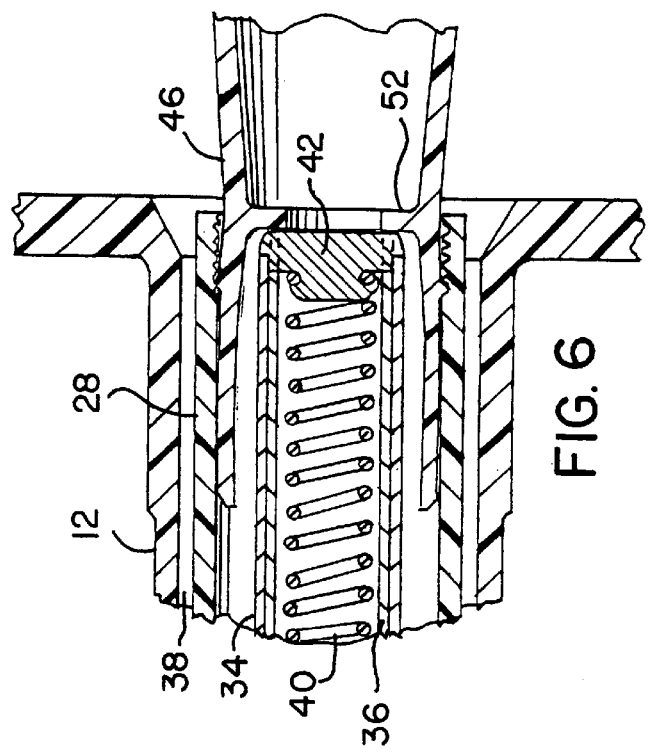
FIG. 6 is an enlarged fragmentary cross-sectional view of the rear end of the syringe with a flange of the plunger being pressed against an inner tubular member to move it toward the front end of the syringe to release the needle and needle housing for retraction into the interior of the syringe.
Figure 5:
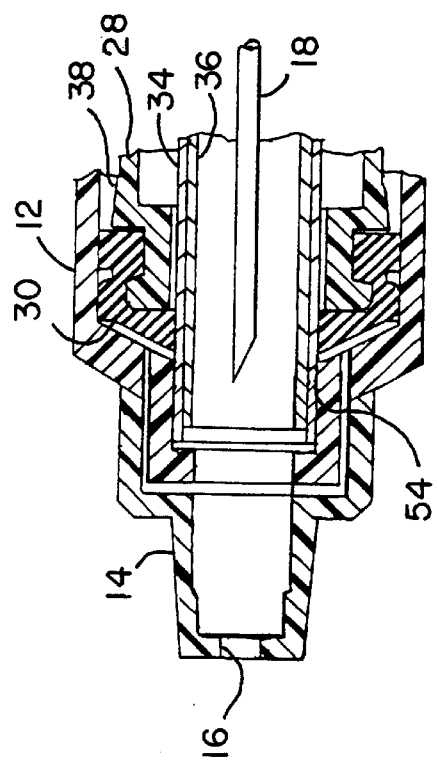
FIG. 5 is an enlarged fragmentary cross-sectional view of the front end of the syringe with the needle in a retracted position similar to that in FIG. 1.
Figure 9:
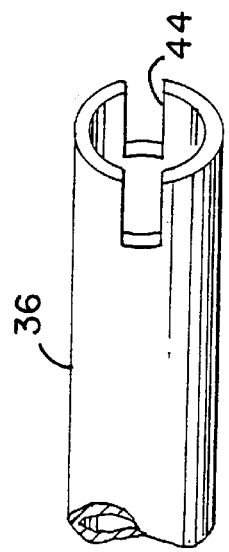
FIG. 9 is a fragmentary perspective view of the inner tube of the assembly shown in FIG. 8 showing the end slot for retaining the spring retaining clip.
Figure 8:
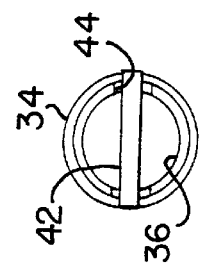
FIG. 8 is a rear end view of a tube assembly with a spring retaining clip for retaining the rear end of a spring for retracting the needle.
Figure 7:
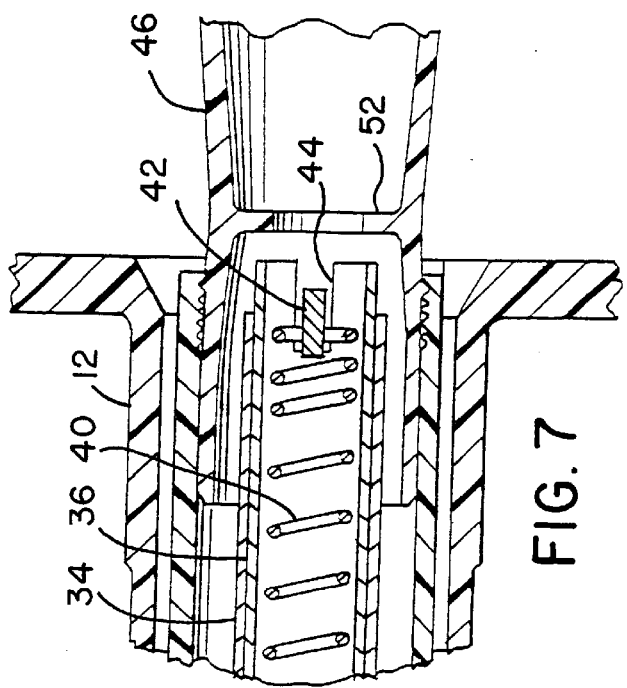
FIG. 7 is a fragmentary cross-sectional view taken on line 7—7 of FIG. 3.
Figure 11:
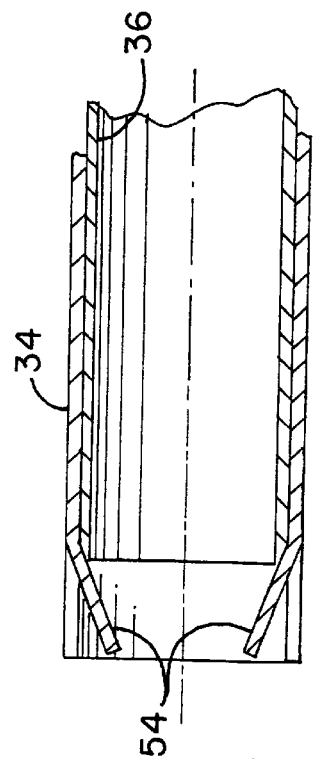
FIG. 11 is a fragmentary axial cross-sectional view of the tube assembly including an outer tube with inwardly bent needle retaining tabs and inner tube which forces the tabs outwardly when moved to the left against the tabs.
Figure 10:
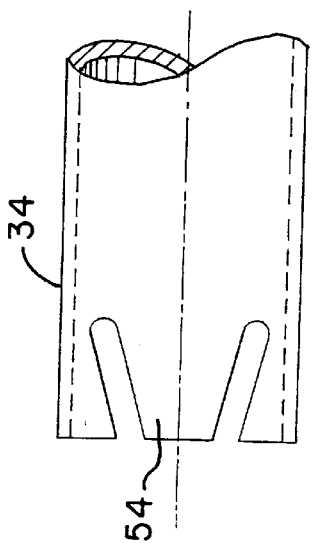
FIG. 10 is a fragmentary side elevational view of an outer tube member showing tabs for retaining the needle and needle assembly in the front end of the syringe barrel when the needle is in the protruding position as shown in FIGS. 1 and 2.

The tension spring 40 is shown diagrammatically in FIGS. 4 and 6 with some space between the coils merely for drawing clarity. In actual operation, when the needle is retracted the spring coils are are in contact with each other. This is due to the preloaded stress built into the spring during manufacturing. The spring 40 is designed to remain under constant tension even in the fully retracted position, thereby holding the needle securely in the retracted position.

The embodiment shown in FIGS. 12 through 14 is a syringe 60 which has a barrel 62 having a front end cap 64 having a center hole 66 through which a needle 68 projects. The needle 68 is carried by a needle housing 72 and together they form a needle assembly 74. A plunger 78 is axially moveable within the barrel 62 and has an annular seal ring 80 which seals against the interior wall of the barrel 62.

The barrel, the plunger and the needle assembly of this embodiment of FIGS. 12 through 14 are essentially the same as those as in the embodiment of FIGS. 1 through 3. The primary difference in this embodiment is that it uses a compression spring to retract the needle 68 instead of a tension spring. Instead of an assembly of two concentric tubes to receive the spring and to house the needle, when retracted, this embodiment uses a single tube 84.

The needle housing 72 has an elongated hollow extension 86 which extends rearwardly to the approximate longitudinal center of the tube 80. In this embodiment the needle housing 72 is made preferably of a plastic material with sufficient rigidity to maintain the spring 90 in a compressed position when the needle 68 is protruding as shown in FIGS. 12 and 13. The front end of the tube 84 has an inwardly turned flange 92 which engages the front end of the spring 90 and the extension 86 has a radially outwardly extending flange 94 which engages the rear end of the spring 90.

The needle assembly 74 is held in the protruding position with the spring 90 compressed by a rigid latch pin 96 which lies inside the tube 84 and extends from the rear end of the extension 86 to a short distance beyond the rear end of the tube 84. The latch pin 96 has a catch member 98 which engages an inwardly bent tab 100 at the rear end of the tube 84. The front end of the latch pin has an offset portion 102 which engages the rear end of the extension 86 and holds the extension and spring in the compressed position within the tube 84.

As shown in FIG. 14 the latch pin 96 has a tapered end portion 104 which extends through a hole 106 in a flange 108 of a rear end cap 110.

The end cap 110 is telescopingly mounted in the plunger 78 in the same manner as the end cap 46. It has a similar series of serrations 112 which are engaged by an annular rib 114 on end cap 110.

In operation, the plunger 78 is depressed to expel the fluid from the barrel 62 and once the front end of the plunger 78 contacts the front end of the barrel and cannot move any further, the end cap 110 moves axially forward inside the plunger 78 and causes the edges of the hole 106 to bear against the tapered end portion 104 in a cam action and thereby causes the latch pin to move toward the center of the tube 84 and release the engagement of the offset portion 102 from the rear end of the extension 86. As soon as latch pin 96 no longer bears against the end of extension 86, this releases the extension 86 to be propelled rearwardly in the tube 84 which simultaneously retracts the needle 68 into the tube 84. The extension 86 has a hollow opening 88 which receives the latch pin 96 as the extension 86 slides rearwardly in the tube 84.

In the interest of simplicity a drawing figure of this embodiment with the needle in the retracted position has not been shown, however, in such a drawing, the needle 68 would be retracted to a location similar to the needle 18 shown in FIG. 4, the rear end of the extension 86 would be near the rear end of tube 84 and the latch pin 96 would be inside the hollow opening 88 in the extension 86.

From the previous descriptions of the two embodiments shown herein it should be recognized that they both function in the same manner when an injection is given. In both embodiments, the plunger is depressed to expel the medication fluid from the syringe and once the plunger bottoms out or contacts the front of the barrel and can move no farther, the end cap telescopes a short distance into the plunger and releases the needle assembly so that it is retracted either by means of a tension spring as shown in FIGS. 1 through 3 or a compression spring as shown in FIGS. 12 and 13. With either embodiment, the user of the syringe performs the same manipulation to give the injection, by merely pressing the plunger until it bottoms out in the barrel then applying additional pressure to effect automatic retraction of the needle.

It can be seen that other needle retraction means can be used without departing from the scope of the inventions as long as the syringe uses a hollow plunger with a means of hydraulically sealing off the interior of the plunger from the fluid chamber of the syringe.

It should also be recognized that the detailed contours and proportions of the various components can vary from some of the illustrations shown in the drawings and the components can be made from various alternative materials from those disclosed herein without departing from the scope of the invention. These and various other modifications can be made in the embodiments shown and described herein without departing from the scope of the invention.

We claim:

1. A safety medical syringe comprising:

a hollow barrel for containing a fluid having a rear end opening and a front end opening and a fluid chamber therein extending between said openings;

a plunger mounted in the fluid chamber of the barrel and axially moveable back and forth between the front and rear end opening of the barrel, for the intake and expulsion of fluid from the fluid chamber, the plunger having a front end sealing means engaging wall surfaces of the barrel within the fluid chamber to prevent fluid from leaking out of the rear end of the barrel, and the plunger having a rear end portion extending out of the rear end opening of the barrel;

a cylindrical needle container, having a front and rear end thereof, the container being attached to the barrel in hydraulically sealed relationship from the fluid chamber to prevent fluid from the fluid chamber from entering the needle container;

a hollow needle temporarily mounted at the front end of the needle container and protruding beyond the front end of both the needle container and the barrel;

the barrel and needle defining a fluid path means between the fluid chamber and the interior of the hollow needle to permit fluid to flow from the fluid chamber through the needle when the plunger is moved toward the front end of the barrel;

bias means within the needle container urging the needle to retract toward the rear end of the needle container;

a retaining means on the needle container for preventing the needle from retracting into the needle container until fluid has been expelled from the fluid chamber; and a release means on the needle container for releasing the retaining means to permit the bias means to retract the needle into the needle container after the fluid has been expelled from the fluid chamber.

2. A syringe as claimed in claim 1 wherein the needle container is comprised of an inner tube and an outer tube, each tube having a front end and a rear end, said tubes being in telescoping concentric relationship with each other, the outer tube being fixedly attached to the front end of the barrel, the inner tube being axially moveable with respect to the outer tube.

3. A syringe as claimed in claim 2 wherein the outer tube has a needle retaining means at its front end which prevents the needle from being retracted into the needle container.

4. A syringe as claimed in claim 3 wherein the needle retaining means is a plurality of detent tabs bent radially inwardly to engage a needle mounting plug and prevent the bias means from retracting the needle and mounting plug into the needle container.

5. A syringe as claimed in claim 3 wherein the front end of the inner tube when moved axially against the needle retaining means releases the needle retaining means to permit the bias means to move the needle into a retracted position within the needle container.

6. A syringe as claimed in claim 2 wherein at least one of the needle container tubes is made of metallic material.

7. Syringe as claimed in claim 6 wherein the metallic material is brass.

8. Syringe as claimed in claim 6 wherein the metallic material is aluminum.

9. Syringe as claimed in claim 6 wherein the metallic material is stainless steel.

10. A syringe as claimed in claim 6 wherein a polymeric coating is applied to at least the outside of the outer tube of the needle container.

11. A syringe as claimed in claim 2 wherein both of the tubes of the needle container are made of metallic material.

12. A syringe as claimed in claim 5 wherein the inner tube is moved axially against the needle retaining means by pressure from the plunger after the plunger has contacted the front end of the barrel.

13. A syringe as claimed in claim 12 wherein the inner tube is contacted by an end cap on the rear end of the plunger, which end cap is axially moveable with respect to a cylindrical body portion of the plunger.

14. A syringe as claimed in claim 13 including detent means on adjacent portions of the end cap and body of the plunger to provide resistance to relative axial movement between the end cap and body, such resistance being overcome by continuing pressure on the end cap after the front end of the plunger has contacted the front end of the barrel.

15. A syringe as claimed in claim 14 wherein the detent means comprises a series of circumferential grooves on one of the plunger parts engaged by at least one circumferential rib on the other plunger part.

16. A syringe as claimed in claim 15 wherein the grooves are of such a progressively changing dimension or engage with such a progressively increasing number of ribs as to provide progressively increased resistance to relative axial movement between the plunger body and the plunger end cap.

17. A syringe as claimed in claim 1 wherein the needle container is mounted concentrically within the barrel on a common axis with the barrel, and wherein the plunger is of annular shape and is positioned in the annular fluid chamber concentrically with the barrel and the needle container.

18. A syringe as claimed in claim 17 wherein the plunger has an annular seal means at the front end thereof which seals against the adjacent wall surfaces of both the barrel and the needle container.

19. A safety medical syringe as claimed in claim 1 wherein the bias means is a tension spring within the needle container having one end attached to a mounting plug holding the needle and the other end attached at the rear end of the needle container, said spring being under constant tension until the release means is actuated and the needle is retracted into the needle container.

20. A safety medical syringe as claimed in claim 1 wherein the bias means is a compression spring within the needle container.

21. A safety medical syringe as claimed in claim 20 wherein the needle container is a single cylindrical member and the retaining means is a releasable latch mechanism located inside the needle container.

22. A safety medical syringe comprising:
- a hollow elongated barrel having a rear end opening and a front end opening;
- a cylindrical needle container mounted within the barrel and attached to the barrel; the barrel and needle container each having cylindrical walls spaced apart from each other to form a fluid chamber therein extending between the rear end opening and front end opening of the barrel;
- the needle container being attached to the barrel in hydraulically sealed relationship to prevent fluid from the fluid chamber from entering the interior of the needle container;
- a plunger mounted in the fluid chamber of the barrel and axially moveable back and forth between the front and rear end opening of the barrel, for the intake and expulsion of fluid from the fluid chamber, the plunger having a front end sealing means engaging wall surfaces of the barrel and needle container which face the inside of the fluid chamber to prevent fluid from leaking out of the rear end of the barrel, and the plunger having a rear end portion extending out of the rear end opening of the barrel;
- a hollow needle temporarily mounted at the front end of the needle container and protruding beyond the front end of both the needle container and the barrel;
- the barrel and needle defining a fluid path means between the fluid chamber and the interior of the hollow needle to permit fluid to flow from the fluid chamber through the needle when the plunger is moved toward the front end of the barrel;
- bias means within the needle container urging the needle to retract toward the rear end of the needle container;
- a retaining means on the needle container for preventing the needle from retracting into the needle container until fluid has been expelled from the fluid chamber; and
- a release means on the needle container for releasing the retaining means to permit the bias means to retract the needle into the needle container after the fluid has been expelled from the fluid chamber.

23. A safety medical syringe comprising:
- a hollow elongated barrel having a rear end opening and a front end opening;
- a cylindrical needle container mounted concentrically within the barrel on a common axis with the barrel and attached to the barrel;
- the barrel and needle container each having cylindrical walls spaced apart from each other to form an annular fluid chamber therebetween extending between the rear end opening and front end opening of the barrel;
- the needle container being attached to the barrel at the front end opening of the barrel in hydraulically sealed relationship to prevent fluid from the fluid chamber from entering the interior of the needle container;
- an annular plunger mounted in the fluid chamber of the barrel and axially moveable back and forth between the front and rear end openings of the barrel, for the intake and expulsion of fluid from the fluid chamber, the plunger having an annular front end sealing means engaging wall surfaces of the barrel and needle container which face the inside of the fluid chamber to prevent fluid from leaking out of the rear end of the barrel, and the plunger having a rear end portion extending out of the rear end opening of the barrel;
- a hollow needle temporarily mounted at the front end of the needle container and protruding beyond the front end of both the needle container and the barrel;
- the barrel and needle defining a fluid path means between the fluid chamber and the interior of the hollow needle to permit fluid to flow from the fluid chamber through the needle when the plunger is moved toward the front end of the barrel;
- bias means within the needle container urging the needle to retract toward the rear end of the needle container;
- a retaining means on the needle container for preventing the needle from retracting into the needle container until fluid has been expelled from the fluid chamber; and a release means on the needle container for releasing the retaining means to permit the bias means to retract the needle into the needle container after the fluid has been expelled from the fluid chamber.

24. A safety medical syringe comprising:

a hollow barrel for containing a fluid, having a rear end opening and a separable needle mounting means at the front end thereof for temporarily securing a hollow needle within the front end of the barrel with the needle protruding forwardly from a front end opening of the barrel until an injection given by the needle has been completed;

a cylindrical tubular needle container mounted concentrically within the barrel on a common axis with the barrel and attached to the barrel;

the barrel and needle container each having cylindrical walls spaced apart from each other to form an annular fluid chamber therebetween extending between the rear end opening and front end opening of the barrel;

the needle container being attached to the barrel at the front end opening of the barrel in hydraulically sealed relationship to prevent fluid from the fluid chamber from entering the interior of the needle container;

the needle and the annular fluid chamber being in hydraulic communication with each other to permit fluid to pass from the fluid chamber through the needle when an injection is given;

an annular plunger having a front end inserted through the rear end opening of the barrel and slidable axially within said barrel to move axially inwardly into the fluid chamber between the barrel and the needle container when pressure is applied to an outwardly extending rear end of the plunger, the front end of the plunger having a seal for engaging adjacent walls of the barrel and needle container to prevent fluid from leaking out of the rear end of the barrel when the plunger is moved inwardly into the barrel;

bias means continually urging the needle and mounting means toward a retracted position within the needle container;

retaining means to temporarily lock the needle and mounting means within the front end of the barrel with the needle protruding from the barrel; and release means to disengage the retaining means and permit the bias means to retract the needle and mounting means into the needle container and to retain the needle in the retracted position within the needle container.

25. A safety medical syringe comprising:

a hollow barrel for containing a fluid having a rear end opening and a front end opening and a fluid chamber therein extending between said openings;

a hollow plunger mounted in the fluid chamber of the barrel and axially moveable back and forth between the front and rear end opening of the barrel, for the intake and expulsion of fluid from the fluid chamber, the plunger containing an axial needle receiving chamber therein and the plunger having a rear end portion extending out of the rear end opening of the barrel;

sealing means on the plunger, engaging wall surfaces of the barrel within the fluid chamber to prevent fluid from leaking out of the rear end of the barrel;

barrier means associated with the plunger to hydraulically separate the fluid chamber from the needle receiving chamber to prevent fluid from the fluid chamber from entering the needle receiving chamber;

a hollow needle temporarily mounted at the front end of the barrel and protruding therefrom;

the barrel and needle defining a fluid path means between the fluid chamber and the interior of the hollow needle to permit fluid to flow from the fluid chamber through the needle when the plunger is moved toward the front end of the barrel;

bias means within the barrel associated with needle urging the needle to a retracted position in the interior of the needle receiving chamber;

retaining means fixed relative to the barrel for preventing the needle from moving into the needle receiving chamber until fluid has been expelled from the fluid chamber; and release means associated with the retaining means for releasing the retaining means to permit the bias means to move the needle into the needle receiving chamber after the fluid has been expelled from the fluid chamber.

26. A safety medical syringe as claimed in claim 25, wherein the needle has a head means secured to a rear end of the needle which removably retains the needle in the front end opening of the barrel.

27. A safety medical syringe as claimed in claim 26, wherein the head means is a resilient annular member which sealingly engages the front end of the barrel to insure that all fluid being expelled from the fluid chamber will only pass through the needle.

28. A safety medical syringe as claimed in claim 25, wherein the barrel has a separate cap element permanently secured to the front end thereof.

29. A safety medical syringe as claimed in claim 25, including means to retain the needle in the needle receiving chamber after it has moved into the retracted position.

30. A safety medical syringe as claimed in claim 25, including a sheath means removably attached to the barrel to cover the needle when in an extended position at the front end of the barrel.

31. A safety medical syringe as claimed in claim 25, wherein the bias means is a compression spring which is compressed to the greatest extent while the needle is protruding from the front end of the barrel in an extended position and wherein the compression is at least partially relieved when the needle moves into the retracted position within the needle receiving chamber.

32. A safety medical syringe as claimed in claim 25, wherein the barrier means is an elongated tubular needle container within the needle receiving chamber attached to the barrel in hydraulically sealed relationship to seal the fluid chamber from the needle receiving chamber.

* * * * *